(12) United States Patent
Chayat

(10) Patent No.: US 9,625,508 B2
(45) Date of Patent: Apr. 18, 2017

(54) VECTOR NETWORK ANALYZER

(71) Applicant: VAYYAR IMAGING LTD., Yehud (IL)

(72) Inventor: Naftali Chayat, Kfar Saba (IL)

(73) Assignee: VAYYAR IMAGING LTD., Yehud (IL)

( * ) Notice: Subject to any disclaimer, the term of this patent is extended or adjusted under 35 U.S.C. 154(b) by 137 days.

(21) Appl. No.: 14/605,084

(22) Filed: Jan. 26, 2015

(65) Prior Publication Data

US 2015/0212129 A1    Jul. 30, 2015

Related U.S. Application Data

(60) Provisional application No. 61/931,708, filed on Jan. 27, 2014.

(51) Int. Cl.
*G01R 27/32* (2006.01)
*A61B 5/05* (2006.01)

(52) U.S. Cl.
CPC .............. *G01R 27/32* (2013.01); *A61B 5/05* (2013.01)

(58) Field of Classification Search
CPC ............ G01R 27/32; G01R 27/28; A61B 5/05
USPC .................................................. 324/637–646
See application file for complete search history.

(56) References Cited

U.S. PATENT DOCUMENTS

| | | | | |
|---|---|---|---|---|
| 6,636,816 B1 * | 10/2003 | Dvorak | ................. | G01R 27/28 324/76.41 |
| 7,034,548 B2 * | 4/2006 | Anderson | ............. | G01R 27/32 324/600 |
| 7,148,702 B2 * | 12/2006 | Wong | .................... | G01R 27/28 324/601 |
| 8,494,615 B2 | 7/2013 | Melamed et al. | | |
| 8,620,238 B2 * | 12/2013 | Chan | .................... | H03G 3/3042 455/126 |

* cited by examiner

*Primary Examiner* — Julian Huffman
*Assistant Examiner* — Michael Konczal
(74) *Attorney, Agent, or Firm* — Browdy and Neimark, PLLC

(57) ABSTRACT

A vector network analyzer (VNA) for analyzing the response of a device under test (DUT), the VNA comprising a plurality of VNA ports configured to be connected to the DUT; a plurality of source ports configured to be connected to the VNA ports; a plurality of couplers for coupling a plurality of coupled signals, wherein said plurality of coupled signals are combined to provide a sum signal; and a receiver configured to receive said forward sum signal.

7 Claims, 4 Drawing Sheets

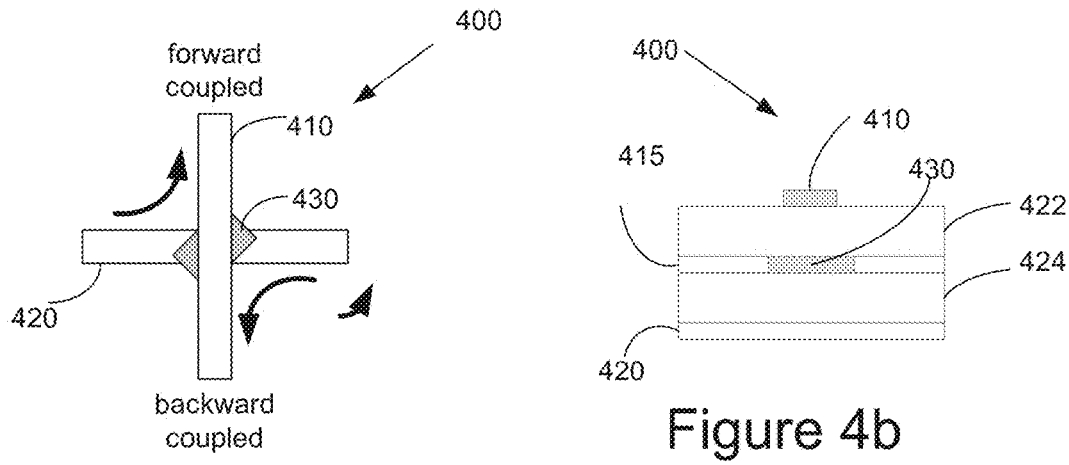
Figure 4a
Figure 4b
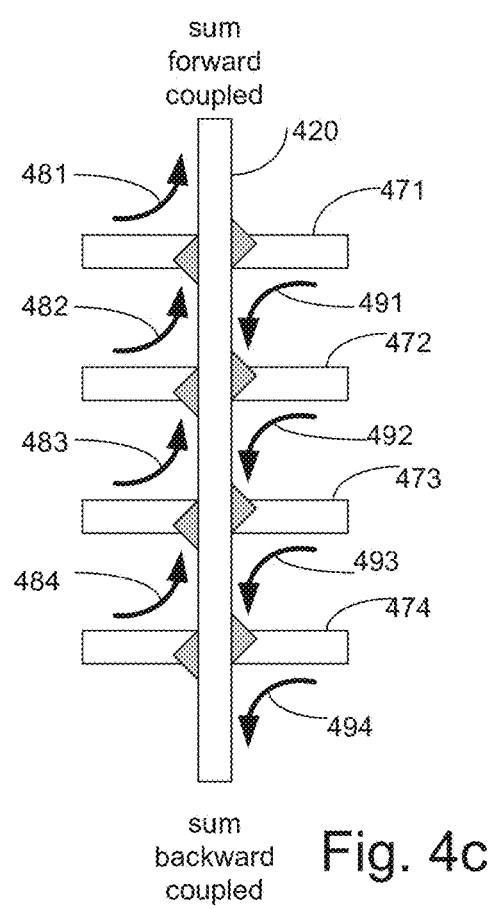
Fig. 4c

VECTOR NETWORK ANALYZER

FIELD OF THE INVENTION

The present invention relates to the field of vector network analyzers, and more particularly to a test set of vector network analyzers.

BACKGROUND OF THE INVENTION

A vector network analyzer (VNA) is a useful instrument for many applications where electrical and/or microwave measurements, such as transmission and reflection properties, are needed. VNA's are usually used where the electrical signals have a high frequency, ranging from (but not limited to) 10 kHz to 100 GHz. Since a VNA can be used to measure complex impedances of circuits at high frequencies, VNAs can be found in many electronic and radio frequency (RF) laboratories, as well as in chip/microwave device or system manufacturing facilities.

A VNA can apply a stimulus sine wave to a device under test (DUT) and perform a series of measurements and calculations. VNAs are often used to characterize two-port networks such as amplifiers and filters, but they can be used on networks with an arbitrary number of ports. A two-port VNA can measure both reflected signals from the DUT and transmitted signals through the DUT. Additionally, the VNA can calculate S-parameters and other related parameters for that DUT. The VNA can repeat this procedure using different frequencies and/or power levels to measure the desired characteristics of the DUT.

The basic architecture of the VNA includes a signal generator, a test set, one or more receivers and a display. A traditional VNA test set 100, as shown in FIG. 1, may include four ports (110, 120, 130 and 140) which may be connected, for example to the DUT ports 150. Each of the test unit ports may be connected to a source transmitter and requires two directional couplers which are connected to two receivers for measuring the reference signal (i.e. R1, R2, R3 and R4) and the received signals (i.e. A, B, C and D). Therefore, according to the prior art solution two receivers are required for each test port. The traditional VNA further includes a number of switches and couplers, such as couplers 115,117,125,127, 135, 137, 145 and 147 located on each branch of the VNA test set 100. The couplers are configured to sample, measure and direct the transmit signal (forward) and the return signals (backward direction) at the VNA (for each direction a single coupler is needed).

The receivers and the transmitters at the VNA are synchronized according to methods known in the field. The testing may be performed simultaneously on all the VNA's ports or separately and alternately at each port.

As illustrated in FIG. 1 the traditional VNA is a complex device which typically occupies a large space, includes multiple elements (such as switching elements connectors and couplers) and is expensive. Moreover, some of the elements are mechanical elements (i.e. coaxial switches) that must be frequently switched, resulting in the decrease of the traditional VNA's reliability. There is a need for an improved, cheap, compact and reliable VNA.

SUMMARY OF THE INVENTION

It is an object of the present invention to provide a VNA that is relatively inexpensive, compact and portable.

It is a further object of the present invention to provide a compact VNA that includes no mechanical switches, a reduced number of elements such as switching elements and directional couplers.

It is a further object of the present invention to provide a compact VNA that includes as few as about half of the receivers of the prior art network analyzers without adding dedicated channels and/or extra physical attenuators/switches and/or complicated external circuitry.

It is a further object of the present invention to provide a VNA that utilizes only two receivers in addition to a single transceiver for each port.

It is another object of the present invention to provide a robust and reliable VNA without being required to add complicated internal or external, physical or mechanical units.

The present invention is particular applicable to systems including antenna arrays which response between different antenna elements needs to be characterized. An example for such system may be a MIMO radar system such as systems recently proposed for breast cancer screening or food product inspection (i.e. for searching foreign objects in food). Examples for such systems may be found in U.S. Pat. No. 8,494,615, entitled "Apparatus and method for Doppler-assisted MIMO radar microwave imaging," which application is incorporated by reference herein in its entirety.

Other objects of the invention will become apparent as the description of the invention proceeds. Thus, according to a first aspect of the present invention there is provided a vector network analyzer (VNA) for analyzing the response of a device under test (DUT), the VNA comprising: a plurality of VNA ports configured to be connected to the DUT; a plurality of source ports configured to be connected to said VNA ports; a plurality of couplers for coupling a plurality of coupled signals, wherein said plurality of coupled signals are combined to provide a sum signal; and a receiver configured to receive said sum signal.

In an embodiment, the plurality of signals are forward coupled signals, and wherein said plurality of forward coupled signals are combined to provide a forward sum signal.

In an embodiment said plurality of signals are backward coupled signals, and wherein said plurality of backward coupled signals are combined to provide a backward sum signal.

In an embodiment the vector network analyzer further comprises a second receiver.

In an embodiment wherein the second receiver is configured to receive said backward sum signal.

In an embodiment said couplers are directional couplers, and wherein the forward coupled signals appear at coupled arms of said directional couplers.

In an embodiment said couplers are directional couplers, and wherein the backward coupled signals appear at coupled arms of said directional couplers.

In an embodiment the coupled arms of said directional couplers are cascaded to form a summing line; and the two receivers are connected to the ends of said summing line.

In an embodiment at least one of said couplers comprise two crossed transmission lines, said transmission lines are configured to form a coupling element between said lines.

Prior to the detailed specification of the invention being set forth it may be helpful to set forth definitions of certain terms that will be used hereinafter.

The term "Directional Coupler" as used herein and through the specification and claims should be understood to encompass a coupler which includes four-port circuits where one port is isolated from the input port. All four ports are (ideally) matched, and the circuit is (ideally) lossless. Directional couplers can be realized in microstrip, stripline, coax and waveguide. They are used for sampling a signal, sometimes both the incident and reflected waves. Directional couplers generally use distributed properties of microwave circuits; the coupling feature is generally a quarter (or multiple) quarter-wavelengths. At lower frequencies, transformer-based directional couplers are available.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4a and 4b—show a top view and a side view of a 'hole coupler' constructed according to the principles of the present invention; and FIG. 4c shows an embodiment of a number of 'hole coupler' connected to one another, constructed according to the principles of the present invention.

DETAILED DESCRIPTION OF THE INVENTION

A better understanding of the present invention is obtained when the following non-limiting detailed description is considered in conjunction with the following figures.

The present invention relates to the field of vector network analyzers, and more particularly to a test set of vector network analyzers.

The present invention provides a device and method for measuring one or more transmitted and a received signals provided, for example by a VNA including at least two ports and a plurality of couplers, by utilizing a combiner, such as single sum line, configured to accumulate the transmitted and received signals, thus avoiding the need to provide dedicated receivers for each of the network analyzer ports.

Network Analyzer Architecture

Figure 2:
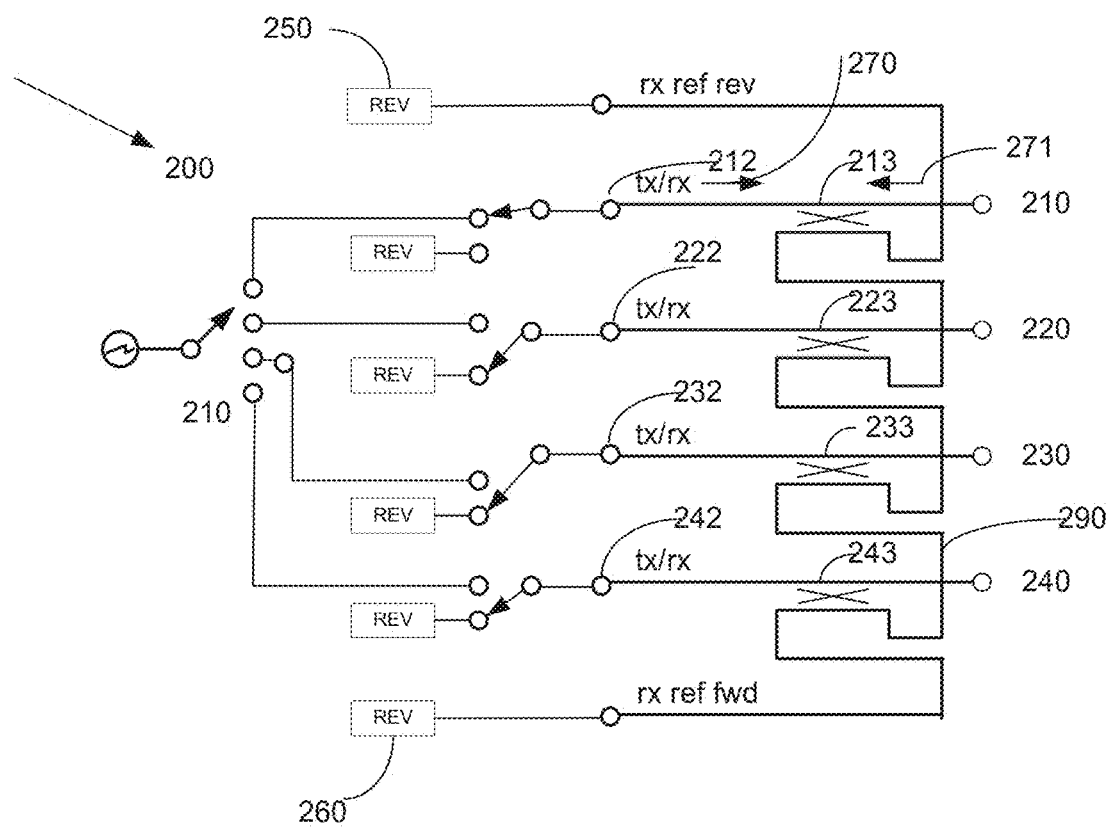
FIG. 2—shows a simplified block diagram of an RF vector network analyzer, constructed according to the principles of the present invention.

According to one embodiment of the invention, as shown in FIG. 2, a VNA 200 comprises a number of ports, such as ports 210, 220, 230 and 240 configured to be connected, for example to the ports of a DUT or a measuring device such as an antenna array. The ports 210, 220, 230 and 240 are further connected respectively to a plurality of Tx/Rx (transceiver, transmit/receive) ports 212, 222, 232, 242. The VNA 200 further comprises a plurality of couplers, such as directional couplers 213, 223, 233 and 243 respectively connected to tx/rx 212, 222, 232, 242. In an embodiment of the invention the transmitted or received (e.g. forward or backward) coupled signals appear at coupled arms of the directional couplers.

As illustrated in FIG. 2 the couplers may be cascaded to form a summing line, for example by a sum line combiner or bus 290 to accumulate one or more sampled signals (e.g. transmitted and/or received) received, for example by receivers 250 and 260.

For example, according to some embodiments of the invention, a transmitted (e.g. forward) signal 270 transmitted by transmitter 222 may be sampled by one of the couplers, such as coupler 223 and may be forwarded by sum line 290 to receiver 260. Respectively, a received (e.g. backward) signal 271 received at port 220 may be sampled by coupler 223 and forwarded through sum line 290 to receiver 260.

Figure 1:
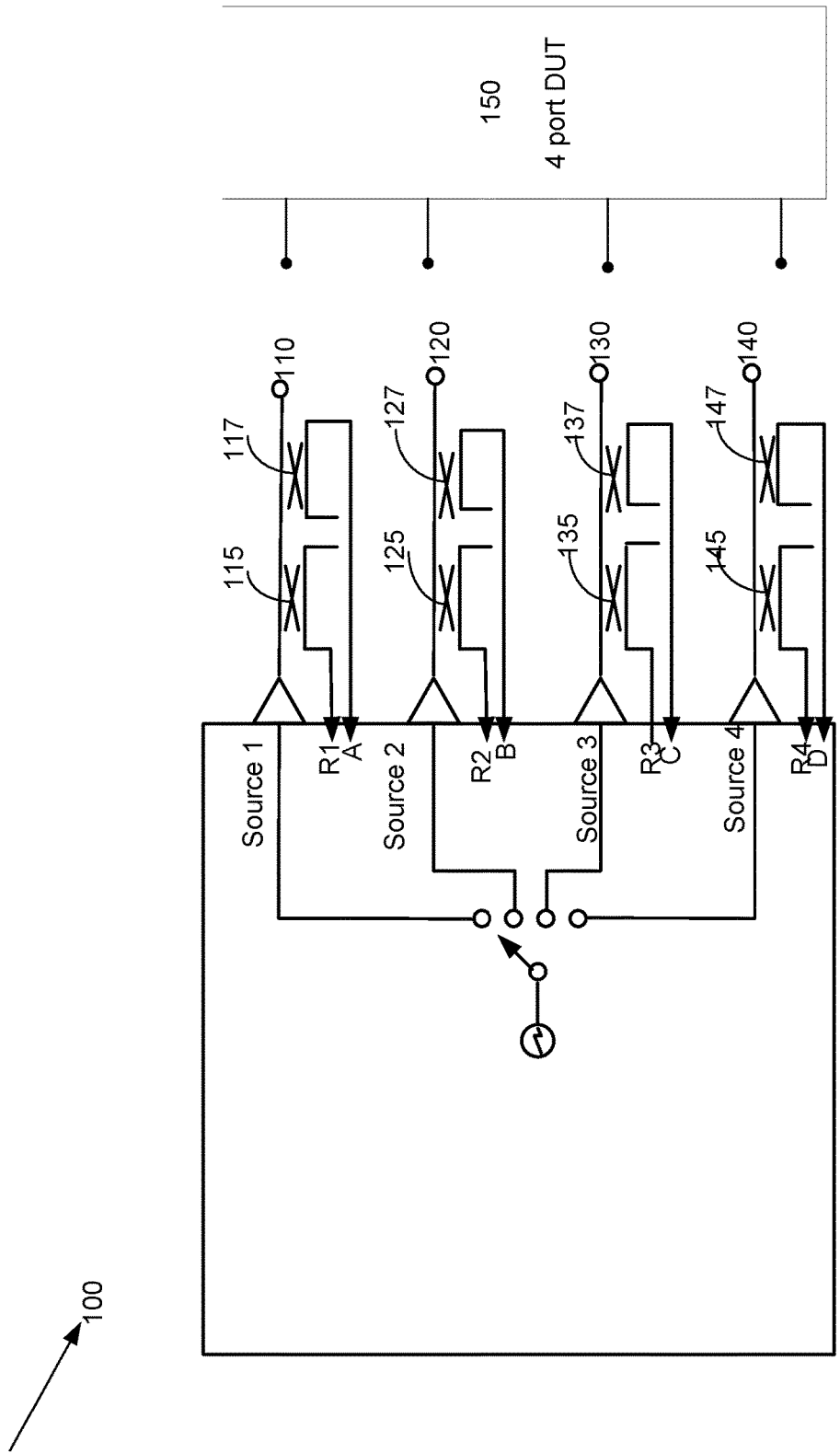
FIG. 1—shows a simplified block diagram of an RF vector network analyzer test set according to the prior art solutions.

As shown in FIG. 2 the number of dedicated receivers needed for constructing the present invention's network analyzer is only two, a first receiver for receiving the sampled forward signals and a second receiver for receiving the received signal, while according to the prior art solution, as shown in FIG. 1 at least two dedicated receivers are needed for each port. Therefore, while according to the prior art, a traditional VNA comprising 4 ports must include at least 8 receivers (i.e. 2 receivers for each port), the present invention provides a simple VNA architecture with only two dedicated receivers needed for receiving the sampled signals transmitted and received by the 4 ports.

Although VNA 200 as illustrated in FIG. 2 by way of example includes two receivers 250 and 260 for receiving respectively a forward sum signal and a backward sum signal some embodiments of the VNA may include a single receiver and the VNA may be configured to sum only forward signals or backward signals.

The unique and compact architecture of the VNA's test set as illustrated in the present invention may be manufactured as a 20×40 mm 3D chip or firmware including two sum lines for coupling the transmitted and received signal at the VNA, sandwiched between two ground planes.

According to another embodiment of the invention, a number of self calibration methods are performed on the VNA to eliminate distractions on the VNA caused for example, by unwanted return and forward signals from the VNA's port coupled to the sum line at the VNA's ports.

VNA Calibration

For each given transmitting port out of N ports, the N+1 received signals (the N−1 receivers at the non-transmitting ports and the two receivers at the ends of the summing coupled line) are linear combinations of a reference transmitter signal and the N incoming signals. The linear relation can be mathematically described as a multiplication by a matrix. As a result, the transmitted signal and the N received signals can be reconstructed from the received signals by multiplication with an inverse matrix. In order to estimate the elements of the transfer matrix that needs to be inverted, calibration procedure similar to the short-open-load-line (SOLT) VNA calibration may be used. A variety of calibration techniques directly applicable to the multiport system according to current invention are described, for example, in a book by Joel P. Dunsmore, "Handbook of Microwave Component Measurements, with advanced VNA techniques", Willey, 2012, which is incorporated herein by reference in its entirety.

Use in a Microwave Imaging System

An exemplary use of a VNA of the present invention is in a microwave imaging system, in which response needs to be measured between multiple antenna pairs. The antennas are connected to the ports of a VNA for obtaining the response measurements. The measured responses are then used in reconstructing the properties of the scene in front of the antenna array. The N antennas composing the antenna array serve as a N-port device-under-test (DUT) for the N-port vector network analyzer (VNA). Microwave imaging systems may be composed of tens of antennas. In view of a large number of antenna ports, it is of utmost interest to use a reduced number of receiver ports, while measuring both transmission and reflection coefficient of each antenna.

Couplers

As mentioned above the VNA of the present invention may include a plurality of directional couplers. It is further an object of the present invention to provide one or more dedicated directional couplers, enabling a uniform coupling throughout the entire signal bandwidth.

It is another object of the present invention to provide compact and reliable couplers, to enable easy and smooth cascading of the couplers.

Two Lines Coupling

Figure 3A:
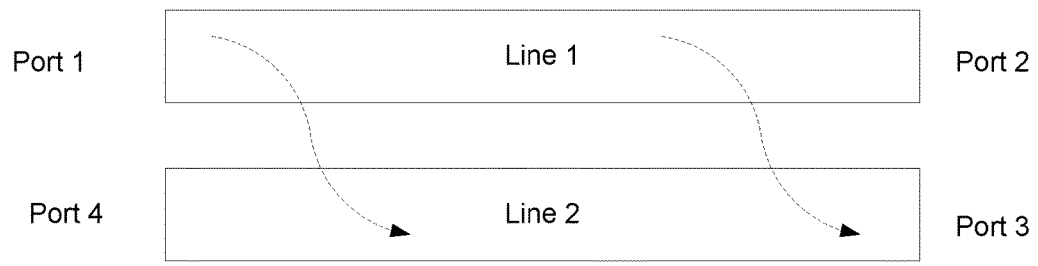
FIGS. 3a and 3b—shows an example demonstrating a coupling of two lines according to the principles of the prior art.
Figure 3B:
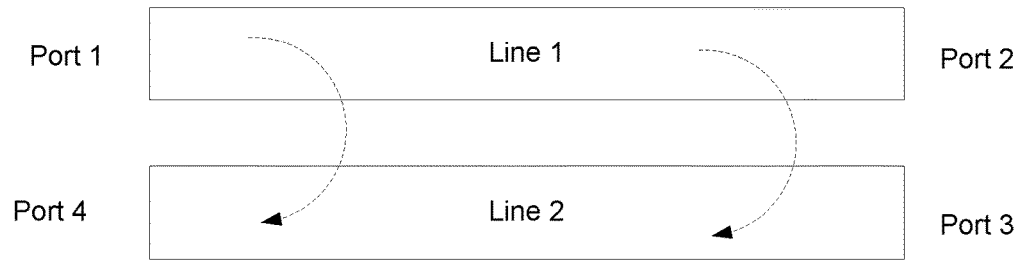

Adjacent transmission lines exhibit both electric and magnetic coupling between the lines. When the electrical and magnetic coupling coefficients are properly balanced, the coupling between the lines exhibits directional characteristics. The directional coupling manifests itself in that signals propagating in one direction on the first line are coupled predominantly to a certain direction on the second line, while the signals on the first line propagating in the second direction are coupled predominantly to the opposite direction on the second line. As shown in FIG. 3a, energy that propagates down transmission line 1 starts a parallel wave down transmission line 2, while in the backward, or reverse coupling, energy that propagates down transmission line starts a reverse wave down transmission line 2, as shown in FIG. 3b. Microstrip or stripline couplers are backward wave couplers because they rely on coupled lines.

In general, a result of the coupling is: a) electric coupling, which will start an inverse parallel current down transmission line 2 b) magnetic coupling, which will induce a current at the same direction in line 1. Therefore, the magnetic and electric impedance of the coupling will sum up on one direction and subtract at the inverse direction. Once the appropriate coupling coefficient are selected, energy that propagates down transmission line 1 starts a reverse wave down transmission line 2, and energy that propagates up transmission line 1 starts a wave on the same direction down transmission line 2.

Hole Couplers

Reference is now made to FIGS. 4a and 4b illustrating a top view and a side view of a hole coupler 400 according to some embodiments of the invention. According to one embodiment of the invention, the coupler 400 may include two crossed transmission lines, such as microstip line 410 and 420, separated by a common ground plane 415. Dielectric substrates 422 and 424 are typically present between the respective lines 410 and 420 and the groundplane 415. A hole 430, such as elongated hole, an opening or a 'notch' or an orifice is formed in the ground plane 415, for example at the intersection of the microstip lines 410, 420. As a result, the orthogonal microstip lines 410 and 420 which were isolated from one another by the ground planes may now induce to and 'interact' with one another through the 'intermediate' hole 430 formed in the ground plane. The hole 430 is configured to perform the following: a) enable electric coupling between the two microstip lines b) form a magnetic coupling between the lines by virtue of the elongated hole being slant with respect to the two microstip lines. According to some embodiments of the invention the lines impedance may be 50 Ohm (e.g. according to the line width and thickness proportions). The presence of both electrical and magnetic coupling between the microstrip lines gives rise to the directional coupling property, as described, for example, in an article entitled "Criteria for the Design of Loop-Type Directional Couplers for the L Band" by P. P Lombardini, R. F Schwartz and P. J Kelly. Selection of the dimensions of the opening along both axes allows achieving high directivity over a broad frequency range. Similar effect is achieved in stripline architecture, if outermost groundplanes are added to shield the entire structure.

Directional couplers between orthogonal coaxial transmission lines were demonstrated in U.S. Pat. No. 2,735,070 entitled "Directional Coupling of Coaxial Transmission Lines", using a combination of pins, wire loops and orifices as coupling elements. Hole coupler of present invention couples microstrip or stripline lines using a slant orifice alone as a coupling element.

According to another embodiment of the invention, a plurality of 'hole couplers' may be cascaded to one another as shown in FIG. 4C, forming a summing coupled line 480 configured to sum the coupled samples of the transmitted signals, such as forward signals 481, 482, 483, and 484 at lines 471, 472, 473, and 474 and in the opposite direction to sum the coupled samples of the received signals, such as backward signals 491, 492, 493, and 494.

According to another embodiment of the invention, the couplers a VNA test set as shown for example in FIG. 2 may be hole couplers and may be cascaded to form a summing line such as a summing line 480, as illustrated in FIG. 4C.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A vector network analyzer (VNA) for analyzing the response of a device under test (DUT), the VNA comprising:
    a plurality of VNA ports configured to be connected to the DUT;
    a plurality of transmit/receive ports configured to be connected to said plurality of VNA ports;
    a plurality of couplers connected to said plurality of VNA ports and to said plurality of transmit/receive ports, wherein said plurality of couplers are configured to output a plurality of coupled signals, and wherein the coupled arms of said plurality of couplers are cascaded to form a summing line; and
    at least one a receiver, wherein said at least one receiver is connected to at least one end of said summing line.

2. The vector network analyzer according to claim 1 comprising two receivers.

3. The vector network analyzer according to claim 2, wherein the two receivers are connected to both ends of said summing line.

4. The vector network analyzer according to claim 1 wherein said plurality of couplers are directional couplers.

5. The vector network analyzer according to claim 1, wherein a signal at one end of the summing line represents the sum of a forward coupled signals and a signal at the second end of the summing line represents the sum of a backward coupled signals.

6. A vector network analyzer (VNA) for analyzing the response of a device under test (DUT), the VNA comprising:
    a plurality of VNA ports configured to be connected to the DUT;
    a plurality of transmit/receive ports configured to be connected to said VNA ports;
    a plurality of couplers connected to said plurality of VNA ports and to said plurality of transmit/receive ports, wherein said plurality of couplers are configured to output a plurality of coupled signals, and wherein said plurality of coupled signals are combined to provide a sum signal; and
    at least one receiver configured to receive said sum signal and wherein at least one of said couplers comprise two crossed transmission lines, said transmission lines are configured to form a coupling element between said lines.

7. A vector network analyzer (VNA) according to claim 6, wherein said coupling element between said lines is a hole in a ground plane.

* * * * *